(12) United States Patent
Harada et al.

(10) Patent No.: US 10,407,450 B2
(45) Date of Patent: Sep. 10, 2019

(54) HETEROGENEOUS POLYNUCLEAR COMPLEX FOR USE IN THE CHEMICAL DEPOSITION OF COMPOSITE METAL OR METAL COMPOUND THIN FILMS

(71) Applicant: TANAKA KIKINZOKU KOGYO K.K., Chiyoda-ku, Tokyo (JP)

(72) Inventors: Ryosuke Harada, Tsukuba (JP); Toshiyuki Shigetomi, Tsukuba (JP); Shunichi Nabeya, Tsukuba (JP); Kazuharu Suzuki, Tsukuba (JP); Akiko Kumakura, Tsukuba (JP); Tatsutaka Aoyama, Tsukuba (JP); Takayuki Sone, Tsukuba (JP)

(73) Assignee: TANAKA KIKINZOKU KOGYO K.K., Tokyo (JP)

( * ) Notice: Subject to any disclaimer, the term of this patent is extended or adjusted under 35 U.S.C. 154(b) by 13 days.

(21) Appl. No.: 15/558,011

(22) PCT Filed: May 9, 2016

(86) PCT No.: PCT/JP2016/063694
§ 371 (c)(1),
(2) Date: Sep. 13, 2017

(87) PCT Pub. No.: WO2016/181917
PCT Pub. Date: Nov. 17, 2016

(65) Prior Publication Data
US 2018/0079764 A1    Mar. 22, 2018

(30) Foreign Application Priority Data
May 12, 2015 (JP) .................. 2015-096980

(51) Int. Cl.
| | |
|---|---|
| *C07F 13/00* | (2006.01) |
| *C07F 15/00* | (2006.01) |
| *C23C 16/16* | (2006.01) |
| *C07F 15/06* | (2006.01) |
| *C07F 19/00* | (2006.01) |
| *C07C 251/08* | (2006.01) |
| *C23C 16/18* | (2006.01) |
| *H01L 21/285* | (2006.01) |
| *H01L 21/31* | (2006.01) |
| *C23C 16/06* | (2006.01) |
| *C23C 16/46* | (2006.01) |
| *H01L 21/02* | (2006.01) |

(52) U.S. Cl.
CPC ........ *C07F 15/0046* (2013.01); *C07C 251/08* (2013.01); *C07F 13/00* (2013.01); *C07F 15/00* (2013.01); *C07F 15/06* (2013.01); *C07F 19/00* (2013.01); *C23C 16/06* (2013.01); *C23C 16/18* (2013.01); *C23C 16/46* (2013.01); *H01L 21/285* (2013.01); *H01L 21/31* (2013.01); *H01L 21/02194* (2013.01); *H01L 21/02271* (2013.01)

(58) Field of Classification Search
CPC .......... C07F 13/00; C07F 15/00; C07F 15/02; C07F 15/04; C07F 15/06; C07F 15/0046; C07F 19/00; C23C 16/06; C23C 16/16; C23C 16/18; H01L 21/02194
See application file for complete search history.

(56) References Cited

U.S. PATENT DOCUMENTS

| | | | |
|---|---|---|---|
| 6,521,561 B1 * | 2/2003 | Jacobsen | ................ B01J 31/183 502/162 |
| 2006/0040822 A1 * | 2/2006 | Shveima | ................. C08F 10/00 502/103 |

(Continued)

FOREIGN PATENT DOCUMENTS

| | | |
|---|---|---|
| JP | 2002-60944 A | 2/2002 |
| JP | 2011-1568 A | 1/2011 |

OTHER PUBLICATIONS

A Ya Yuffa and Georgil V Lisichkin 1986 Russ. Chem. Rev. 55, (9) 825-842.*

(Continued)

*Primary Examiner* — Bret P Chen
(74) *Attorney, Agent, or Firm* — Orrick, Herrington & Sutcliffe LLP; Joseph A. Calvaruso

(57) ABSTRACT

A heterogeneous polynuclear complex for use as a raw material in the chemical deposition of composite metal or composite metal thin films with the below formula. In the formula, $M_1$ and $M_2$ are mutually different transition metals, x is an integer of 0 or more and 2 or less, y is in integer of 1 or more and 2 or less, z is an integer of 1 or more and 10 or less, $R_1$ to $R_4$ are each one of a hydrogen atom and an alkyl group with a carbon number of 1 or more and 5 or less, and $R_5$ is a hydrogen atom, a carbonyl, an alkyl group with a carbon number of 1 or more and 7 or less, an allyl group or an allyl derivative. The heterogeneous polynuclear complex allows a composite metal thin film or a composite metal compound thin film containing a plurality of metals to be formed from a single raw material.

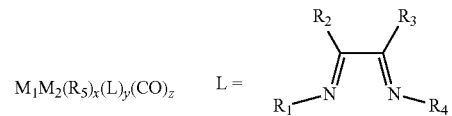

20 Claims, 2 Drawing Sheets

(56) References Cited

U.S. PATENT DOCUMENTS

| | | | |
|---|---|---|---|
| 2008/0033125 A1* | 2/2008 | Solan | B01J 31/1815 526/115 |
| 2012/0091588 A1 | 4/2012 | Miyoshi | |
| 2018/0119274 A1* | 5/2018 | Harada | C07F 13/00 |

OTHER PUBLICATIONS

Yuffa, A. Ya., et al., "Cluster and Polynuclear Heterogenous Metal Complex Catalysts". Russian Chemical Reviews, 55 (9), 1986.*

Rohacova, Jana, et al., "Photofunctional multinuclear rehniunn(I) diimine carbonyl complexes". Dalton Transactions, 2017, 46, 8899-8919.*

Zhivonitko, Vladimir, et al., "Role of Different Active Sites in Heterogeneous Alkene Hydrogenation on Platinum Catalysts Revealed by Means of Parahydrogen-Induced Polarization". The Journal of Physical Chemistry C, 2011, 115, 13386-13391.*

Diez-Gonzalez, Silvia, et al., "Cationic Copper(I) Complexes as Efficient Precatalysts for the Hydrosilyation of Carbonyl Compounds". Organometallics 2006, 25, 2355-2358.*

Adams, Richard D., et al., "Unusual Structures and Reactivity of Mixed Metal Cluster Complexes Containing the Palladium/Platinum Tri-t-butylphosphine Grouping". Accounts of Chemical Research, vol. 42, No. 3, Mar. 2009, 409-418.*

Staal et al., Binuclear Metal Carbonyl DAB Complexes. III. Activation of a C=N Double Bond in $Ru_2(CO)_6(DAB)$ Complexes (DAB=1,4 diazabutadiene), C—C Bond Formation between Two DAB Ligands, Inorganica Chimica Acta, Elsevier BV, vol. 37, 1979, pp. 1485-1487.

Kokkes et at, Photochemistry of Metal-Metal-Bonded Complexes. 1. MLCT photolysis of $(CO)_5MM'(CO)_3(\alpha$-diimine$)$(M, M'=Mn, Re) in 2-MeTHF between 133 and 230 K, Inorganic Chemistry, vol. 24, 1985, pp. 2934-2942.

Kraakman et al., Preparation of Novel Alkylated Ruthenium α-Diimine Complexes: Reactivity toward Carbon Monoxide and Phosphines, Organometallics, American Chemical Society, vol. 11, 1992, pp. 3760-3773.

Nieuwenhuis et al., Photochemistry of the Metal-Metal-Bonded Complexes $[(CO)_5Mn$—$Ru(Me)(CO)_2(\alpha$- diimine$)]$. Crystal Structure of the Photoproduct $[(CO)_4Mn$-$\mu$-$(\sigma(N), \sigma (N'), \eta^2(CN)$-$^iPr$—PyCa$)Ru(Me)(CO)_2]$, Journal of Organometallic Chemistry, Elsevier-Sequoia S.A. Lausanne, CH, vol. 492, No. 2, May 3, 1995, pp. 165-177.

Aarnts et al., Photochemical bond hemolysis in a novel series of metal-metal bonded complexes Ru (E) (E') (CO) 2 (iPr-DAB), Inorganica Chimica Acta, vol. 266, No. 1, Jan. 1, 1997, pp. 37-46.

International Search Report for PCT/JP2016/063694 dated Jun. 7, 2016.

Aarnts, et al., Syntheses, structures and spectroscopic properties of novel inorganometallic complexes Ru $(E)(E')(CO)_2(iPrDAB)$ (E=Cl,E'=SnPh$_3$, PbPh$_3$; E=Me, E'=SnPh$_3$, PbPh$_3$; E=SnPh$_3$, E '=SnPh$_3$, SnMe$_3$, GePh$_3$; E=PbPh$_3$, E'=PbPh$_3$,PbMe$_3$,GePh$_3$; iPr-DAB=N,N'-diisopropyl-1,4-diaza-1,3-butadiene), Inorganica Chimica Acta, 1997, 256, pp. 93-105.

Aarnts, et al., Photochemical bond homolysis in a novel series of metal-metal bonded complexes Ru(E)(E')(CO)$_2$(iPr-DAB), Inorganica Chimica Acta, 1997, 266, pp. 37-46.

Slageren, et al., Influence of the variation of the co-ligands on the electronic transitions and emission properties of [Pt(I)(CH$_3$)$_3$(iPr-DAB)],[Pt(CH$_3$)$_4$(α-diimine)] and [Pt(SnPh$_3$)$_2$(CH$_3$)$_2$(iPr-DAB)]: an experimental and theoretical study, J.Chem.Soc., Dalton Trans., 2002, pp. 218-225.

* cited by examiner

HETEROGENEOUS POLYNUCLEAR COMPLEX FOR USE IN THE CHEMICAL DEPOSITION OF COMPOSITE METAL OR METAL COMPOUND THIN FILMS

TECHNICAL FIELD

The present invention relates to a chemical deposition raw material including a heterogeneous polynuclear complex, which is used for producing a composite metal thin film or a composite metal compound thin film including different kinds of metals by a chemical deposition method such as a CVD method or an ALD method. Specifically, the present invention relates to a chemical deposition raw material which is capable of forming a thin film including a composite metal in one-time film formation and which is capable of forming a film at low temperature (about 200° C.) while having moderate thermal stability.

BACKGROUND ART

In various kinds of devices such as semiconductors, various kinds of metal thin films are used for satisfying the required properties of the devices. As a method for forming these metal thin films, a chemical deposition method such as a CVD method, which is capable of forming a uniform and homogeneous film at a high film formation rate and in conformity with even a three-dimensional shape etc. of a device, is used.

As a metal complex that is a raw material in formation of a metal thin film by the chemical deposition method, a complex including a plurality of ligands such as cyclopentadienyl with one metal as a central metal (nucleus) (hereinafter, referred to as a mononuclear complex) as shown in the following chemical formula 1 is known. A complex including a plurality of metals of the same kind as central metals (hereinafter, referred to as a homogeneous polynuclear complex) as shown in the following chemical formula 2 is also known.

[Chemical Formula 1]

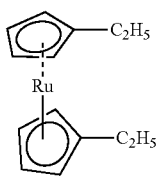

[Chemical Formula 2]

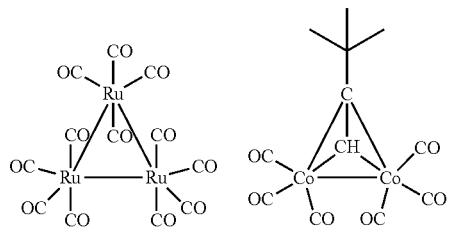

-continued

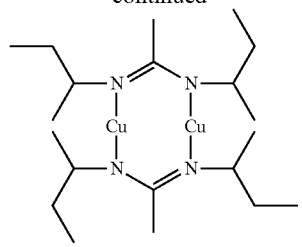

In formation of a metal thin film for use in a device such as a semiconductor by use of the above-mentioned mononuclear complex or homogeneous polynuclear complex as a chemical deposition raw material, a thin film including a plurality of kinds of metals is often applied. In a device having a reduced size and weight, such as a semiconductor, a plurality of metal thin films are applied, and deposited for imparting various kinds of required properties, so that the device is densified and highly integrated while attaining required properties. For example, when copper is used as a wiring material of a semiconductor, a structure is used in which a thin film of MnO, MnSiO and the like as a barrier layer for preventing diffusion of copper, and a thin film of ruthenium or the like as a base for introducing the barrier layer are deposited together.

As an example of forming a thin film including a plurality of metals as described above, mention is made of Patent Document 1, Patent Document 2 and so on. Patent Document 1 suggests that a plurality of mononuclear complexes etc. are provided, and metal thin films are sequentially deposited from the complexes to form a plurality of metal layers each including a single metal. Patent Document 2 suggests that a plurality of mononuclear complexes etc. are mixed beforehand, and dissolved or emulsified to obtain an inert liquid, and from the inert liquid, a composite metal thin film containing a plurality of metals is formed.

RELATED ART DOCUMENT

Patent Documents

Patent Document 1: JP 2011-1568 A
Patent Document 2: JP 2002-60944 A

SUMMARY OF THE INVENTION

Problems to be Solved by the Invention

However, when a plurality of thin films are sequentially formed by use of a plurality of complexes as in Patent Document 1, a large number of steps are required for film formation, condition setting is complicated, much time and labor is needed for quality control of raw materials, and use of a plurality of raw materials causes an increase in cost. When a plurality of metal complexes are mixed beforehand as in Patent Document 2, the complexes have different vaporization properties, and therefore the ratio of metals in the thin film easily varies, so that formation of a homogeneous film becomes difficult. Before film formation, raw materials may react with each other, leading to degeneration.

The present invention has been made in view of the background described above, and provides a chemical deposition raw material which is capable of forming a plurality of kinds of metal thin films in a simple process, and capable of forming a homogeneous thin film, and is easily quality-controlled.

Means for Solving the Problems

As a solution to the problems described above, the present inventors conducted the following studies for synthesizing a complex including a plurality of kinds of metals as central metals in one complex (hereinafter, referred to as a heterogeneous polynuclear complex), and applying the complex as a chemical deposition raw material instead of applying a plurality of complexes having different metal species as in a conventional art.

When a heterogeneous polynuclear complex is applied as a chemical deposition raw material, first a plurality of kinds of metals as central metals should be all deposited in formation of a metal thin film by a chemical deposition method as a required property of the chemical deposition raw material. Preferably, the deposition ratios of a plurality of metals are almost the same. The chemical deposition raw material should also have such a general required property of a chemical deposition raw material that in formation of a thin film by a chemical deposition method, the chemical deposition raw material has thermal stability sufficient to prevent thermal decomposition in a vaporization stage while having a decomposition property which ensures that a film can be formed at low temperature. The present inventors extensively conducted studies on a complex having all the above-mentioned properties, and resultantly arrived at a chemical deposition raw material of the present invention which includes a heterogeneous polynuclear complex having a configuration as described below.

The present invention relates to a chemical deposition raw material for producing a composite metal thin film or a composite metal compound thin film by a chemical deposition method, including a heterogeneous polynuclear complex in which at least a diimine (L) containing two imines and a carbonyl are coordinated to a first transition metal ($M_1$) and a second transition metal ($M_2$) as central metals, the heterogeneous polynuclear complex being represented by the following formula:

[Chemical Formula 3]

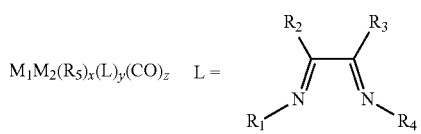

wherein $M_1$ and $M_2$ are mutually different transition metals; x is an integer of 0 or more and 2 or less, y is an integer of 1 or more and 2 or less, and z is an integer of 1 or more and 10 or less; $R_1$ to $R_4$ are each one of a hydrogen atom and an alkyl group with a carbon number of 1 or more and 5 or less; and $R_5$ is a hydrogen atom, a carbonyl, an alkyl group with a carbon number of 1 or more and 7 or less, an allyl group or an allyl derivative.

As described above, the complex in the present invention is a heterogeneous polynuclear complex including a plurality of kinds of transition metals: a first transition metal ($M_1$) and a second transition metal ($M_2$) as central metals of the complex, and to these central metals are coordinated at least a diimine (L) and a carbonyl (—CO) as ligands. When a thin film is formed from the complex by a chemical deposition method, a plurality of metals as central metals are all deposited.

The complex of the present invention has moderate thermal stability because the diimine as a ligand has a relatively strong bonding force with a transition metal, and the carbonyl as a ligand has a relatively weak bonding forth with a transition metal. Since the carbon number of the alkyl group as each of substituents $R_1$ to $R_5$ is arbitrarily designed, the vapor pressure and the melting point can be adjusted.

Hereinafter, the heterogeneous polynuclear complex included in the chemical deposition raw material according to the present invention will be described in detail.

First, x, y and z representing the numbers of ligands ($R_5$), diimines (L) and carbonyls (CO), respectively, in the raw material of the present invention will be described. x is an integer of 0 or more and 2 or less, y is an integer of 1 or more and 2 or less, and z is an integer of 1 or more and 10 or less; Preferably, x is 1 or more and 2 or less, y is 1 or more and 2 or less, and z is 3 or more and 8 or less.

Preferred ranges of the integers that can be selected as x, y and z depend on the kind (valence) of the transition metal and the correlation associated with the value of x. For example, provided that at least one of $M_1$ and $M_2$ is Fe or Ru, preferably, y is 2 and z is 4 to 6 when x is 0, preferably, y is 1 and z is 4 to 7 when x is 1, and preferably, y is 1 and z is 2 to 6 when x is 2.

It is especially preferable that x is 1, y is 1 and z is n+2 as a combination of x, y and z, and mention is made of, for example, a chemical deposition raw material including a heterogeneous polynuclear complex represented by the following formula:

[Chemical Formula 4]

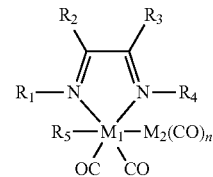

wherein $M_1$ and $M_2$ are mutually different transition metals; n is 3 or more and 6 or less; Each of $R_1$ and $R_4$ is an alkyl group with a carbon number of 1 or more and 4 or less, and each of $R_2$ and $R_3$ is a hydrogen atom, or an alkyl group with a carbon number of 1 or more and 3 or less; and $R_5$ is a carbonyl, or an alkyl group with a carbon number of 1 or more and 4 or less.

$M_1$ and $M_2$ are mutually different transition metals. Examples of the transition metal include titanium (Ti), vanadium (V), chromium (Cr), manganese (Mn), iron (Fe), cobalt (Co), nickel (Ni), copper (Cu), niobium (Nb), molybdenum (Mo), ruthenium (Ru), rhodium (Rh), palladium (Pd), silver (Ag), tantalum (Ta), tungsten (W), rhenium (Re), osmium (Os), iridium (Ir), platinum (Pt) and gold (Au). As the transition metal, Mn, Fe, Co, Ni, Cu, Nb, Mo, Ru, Rh, Ta, W, Ir and Pt are preferable, and Mn, Fe, Co, Ni, Cu, Mo, Ru, W and Pt are especially preferable. As the transition metal as $M_1$, Ru, Mn and Fe are especially preferable, and as the transition metal as $M_2$, Mn, Fe, Co and Ni are especially preferable.

Ligands to be coordinated to central metals will now be described. In the raw material of the present invention, at least a diimine and a carbonyl are coordinated to central metals including two transition metals as in, for example, the following compound. The present inventors arrived at the raw material based on the following grounds regarding the configurations of the central metals and the ligands coordinated to the central metals.

[Chemical Formula 5]

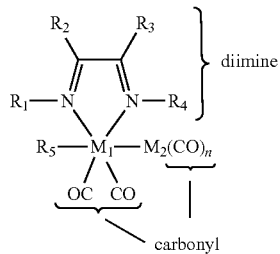

The "diimine (L)" as a ligand refers to a ligand which has a secondary amine (imino group) having a carbon-nitrogen double bond, and includes a conjugated diene including two conjugated double bonds as carbon-carbon bonds. A ligand having two secondary amines as described above tends to improve thermal stability of the complex because nitrogen atoms in two imino groups are strongly bonded to central metals. A diimine compound tends to have a small molecular weight and a low boiling point, is easily evaporated after decomposition, and thus hardly remains as an impurity in a metal film, and in addition to this advantage, the diimine compound can increase the vapor pressure of a complex having the diimine compound as a ligand.

Comparison between the ligands for ease of separation from the central metal shows that the carbonyl (—CO) tends to be more easily separated from the central metal than the diimine (L). Here, when a composite metal thin film is formed by a chemical deposition method, the amount of each transition metal deposited in the thin film often depends on the kind of a ligand coordinated to each transition metal. Of two transition metals, a transition metal having a larger amount of the carbonyl and a smaller amount of the diimine in terms of a ligand tends to be deposited in a larger amount in the formed composite metal thin film. For example, in the case of the following compound that is mentioned as a preferred example in the present invention, the second transition metal $M_2$ to which only the carbonyl is coordinated is apt to be deposited in a larger amount in the composite metal thin film than the first transition metal $M_1$ to which the diimine is coordinated.

[Chemical Formula 6]

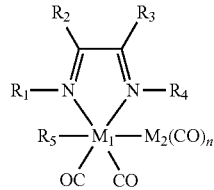

wherein $M_1$ and $M_2$ are mutually different transition metals; n is 3 or more and 6 or less; Each of $R_1$ and $R_4$ is an alkyl group with a carbon number of 1 or more and 4 or less, and each of $R_2$ and $R_3$ is a hydrogen atom, or an alkyl group with a carbon number of 1 or more and 3 or less; and $R_5$ is a carbonyl, or an alkyl group with a carbon number of 1 or more and 4 or less.

Substituents $R_1$ to $R_4$ of the diimine will now be described. $R_1$ to $R_4$ are each one of a hydrogen atom and an alkyl group with a carbon number of 1 or more and 5 or less; and When the carbon chain is excessively long, the vapor pressure of the complex tends to decrease, and in the case of a long-chain alkyl group with a carbon number of more than 5, the complex is difficult to vaporize. Either a linear or branched alkyl group can be applied as each of substituents $R_1$ to $R_4$. For example, when a propyl group or a butyl group is applied, a n-propyl group, an iso-propyl group, a n-butyl group, an iso-butyl group, a sec-butyl group, a tert-butyl group or the like can be applied.

With regard to each substituent, each of $R_1$ and $R_4$ is preferably an alkyl group with a carbon number of 1 or more and 4 or less, especially preferably one of an ethyl group, a propyl group and a butyl group. Each of alkyl groups of $R_1$ and $R_4$ is preferably a branched alkyl group, especially preferably one of an iso (i-)propyl group, a tert-butyl group and a sec-butyl group. Each of $R_2$ and $R_3$ is preferably a hydrogen atom or an alkyl group with a carbon number of 1 or more and 3 or less, especially preferably one of a hydrogen atom, a methyl group and an ethyl group.

The number of ligands $R_5$ is 0 or more and 2 or less, and preferably, one of the ligands $R_5$ is a ligand of $M_1$. $R_5$ is one of a hydrogen atom, a carbonyl, an alkyl with a carbon number of 1 or more and 7 or less, an allyl or an allyl derivative, preferably a carbonyl or an alkyl with a carbon number of 1 or more and 4 or less, especially preferably a carbonyl, methyl ethyl or propyl. Which of a carbonyl and an alkyl is preferred as the ligand $R_5$ depends on the kind of the first transition metal ($M_1$). A carbonyl is especially preferable when $M_1$ is Mn, Co, Rh, Re or Ir, and an alkyl is especially preferable when $M_1$ is Fe, Ru or Os. When the ligand $R_5$ is an alkyl, either a linear or branched alkyl can be applied.

In the complex in the present invention, the total number of carbonyls (CO) is 1 or more and 10 or less, and preferably, the ligand of the first transition metal ($M_1$) has two or three carbonyls. The coordination number (n) of carbonyls as the ligand of the second transition metal ($M_2$) is preferably 4 or 5, and which coordination number is preferred depends on the kind of the second transition metal ($M_2$). The coordination number (n) is especially preferably 5 when $M_2$ is Mn or Re, and the coordination number (n) is especially preferably 4 when $M_2$ is Co, Rh or Ir.

Specific kinds of heterogeneous polynuclear complexes that are preferred for the chemical deposition raw material of the present invention are listed below as examples.

[Chemical Formula 7]

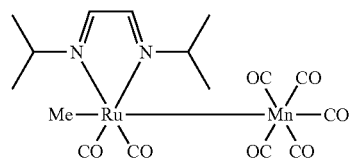

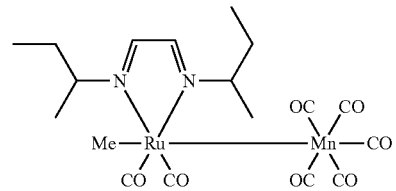

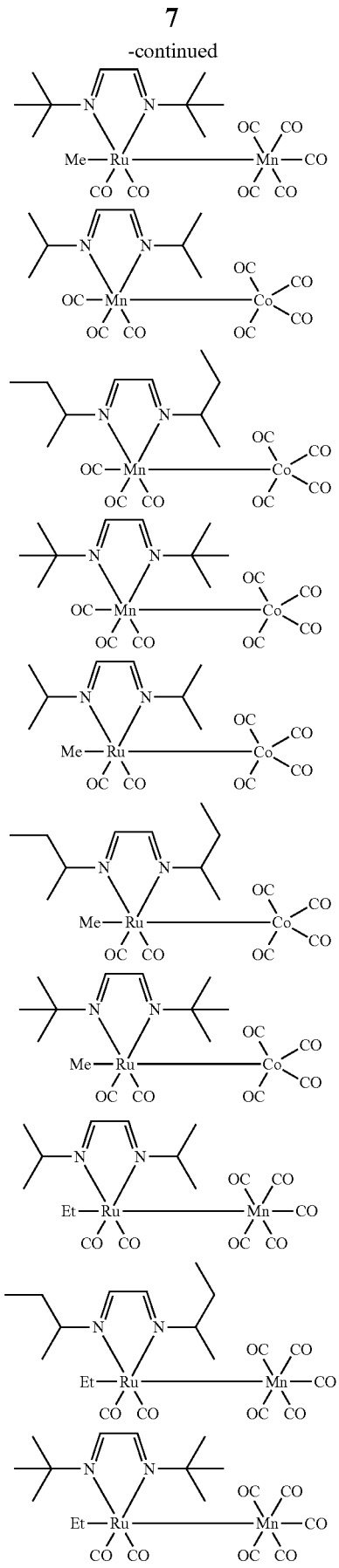
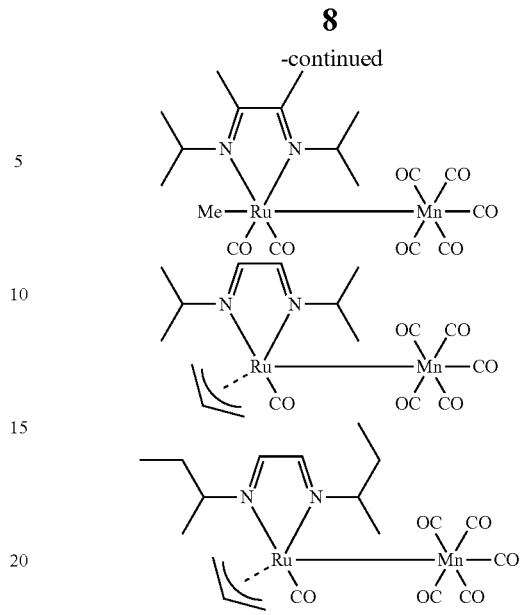

The chemical deposition raw material of the present invention described above can be produced in the following manner: a starting raw material that is a diazabutadiene derivative with the first transition metal ($M_1$) as a central metal is reacted with a complex to which a plurality of carbonyls are coordinated with the second transition metal ($M_2$) as a central metal.

The present chemical deposition raw material is useful for formation of a composite metal thin film by a CVD method. This thin film formation method includes preparing a reaction gas by vaporizing a raw material including a heterogeneous polynuclear complex, introducing the reaction gas to a substrate surface, and decomposing the complex to deposit a plurality of metals. In this method, the heterogeneous polynuclear complex according to the present invention is used as a raw material.

The reaction atmosphere during formation of the thin film is preferably a reducing atmosphere, and therefore preferably, hydrogen or ammonia is introduced as a reaction gas. The heating temperature during film formation is preferably 150° C. to 350° C. When the heating temperature is lower than 150° C., the film formation hardly proceeds, and thus a required thickness is hard to obtain. When the heating temperature is higher than 350° C., formation of a uniform thin film is difficult.

Advantageous Effects of the Invention

With the chemical deposition raw material according to the present invention, a composite metal thin film or a composite metal compound thin film containing a plurality of metals can be formed from a single raw material as described above. The raw material of the present invention has a high vapor pressure, is capable of producing a thin film at low temperature, has moderate thermal stability, and is thus suitable for film formation by a chemical deposition method.

DESCRIPTION OF EMBODIMENT

Figure 1:
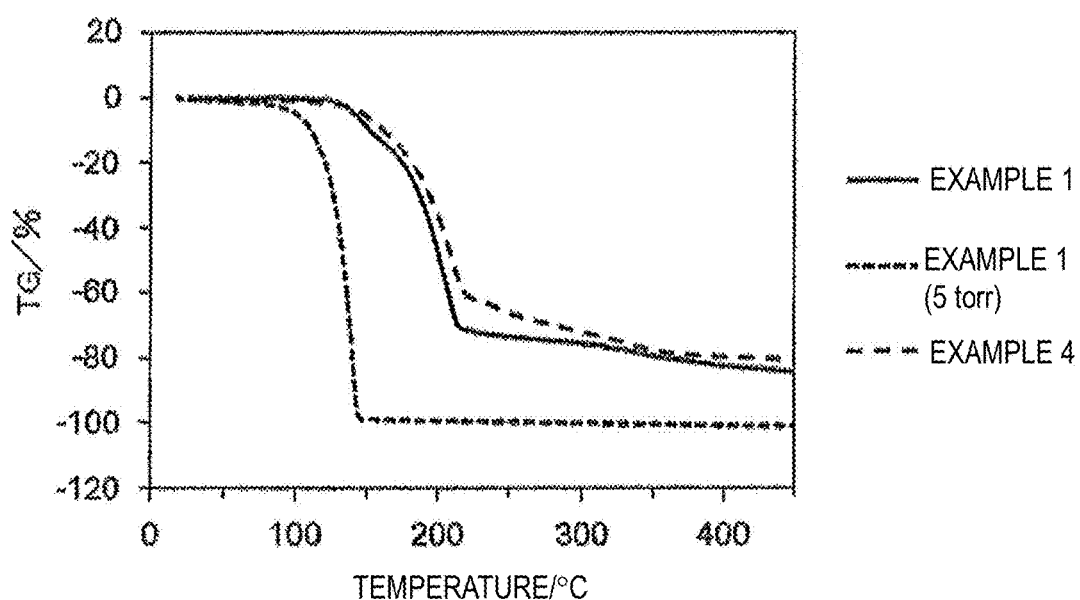
FIG. 1 illustrates a TG curve of a metal complex produced in an embodiment.

Hereinafter, the best embodiments in the present invention will be described.

In the embodiments, the following four kinds of complexes were synthesized. Synthesized complexes were each evaluated for physical properties, and subjected to a film formation test as a chemical deposition raw material.

[Chemical Formula 8]

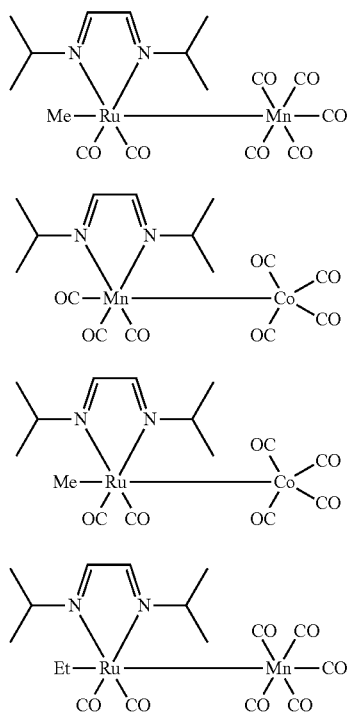

Example 1

Example 2

Example 3

Example 4

EXAMPLE 1

A heterogeneous polynuclear complex (pentacarbonyl[dicarbonyl(N,N'-diisopropyl-1,4-diazabutadiene)methylruthenium]manganese (Mn—Ru)) having ruthenium as a first transition metal and manganese as a second transition metal was produced. The synthesis reaction formula is as described below. Hereinafter, the production process will be described in detail.

[Chemical Formula 9]

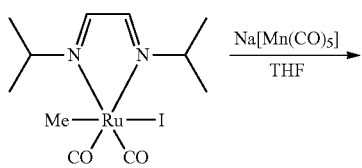

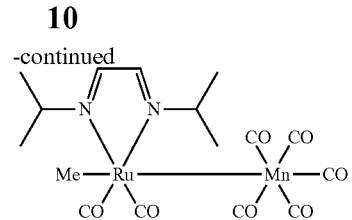

1.95 g (5 mmol) of decacarbonyldimanganese and 0.23 g (10 mmol) of metal sodium were added in a flask containing 250 ml of tetrahydrofuran. The solution was stirred at room temperature for 24 hours, a solution obtained by dissolving 4.39 g (10 mmol) of dicarbonyliodo(N,N'-diisopropyl-1,4-diazabutadiene)methylruthenium in 250 ml of tetrahydrofuran was then added, and the mixture was stirred at room temperature for 4 hours. After completion of the reaction, the reaction product was concentrated to obtain a muddy reaction mixture. The reaction mixture was extracted with hexane, and purified by column chromatography with alumina as a carrier and hexane as an eluent. Sublimation purification was performed to obtain 3.30 g (6.5 mmol) of pentacarbonyl[dicarbonyl(N,N'-diisopropyl-1,4-diazabutadiene)methylruthenium]manganese (Mn—Ru) as a specified substance (yield: 65%).

EXAMPLE 2

A heterogeneous polynuclear complex (tricarbonyl(N,N'-diisopropyl-1,4-diazabutadiene)(tetracarbonylcobalt)manganese (Co—Mn)) having manganese as a first transition metal and cobalt as a second transition metal was produced. The synthesis reaction formula is as described below. Hereinafter, the production process will be described in detail.

[Chemical Formula 10]

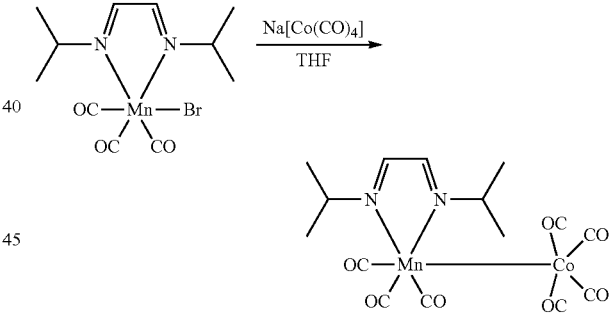

1.71 g (5 mmol) of octacarbonyldicobalt and 0.23 g (10 mmol) of metal sodium were added in a flask containing 250 ml of tetrahydrofuran. The solution was stirred at room temperature for 24 hours, a solution obtained by dissolving 3.60 g (10 mmol) of bromotricarbonyl(N,N'-diisopropyl-1,4-diazabutadiene)manganese in 250 ml of tetrahydrofuran was then added, and the mixture was stirred at room temperature for 4 hours. After completion of the reaction, the reaction product was concentrated, and then extracted with hexane. After recrystallization from hexane at −30° C., sublimation purification was performed to obtain 1.13 g (5.0 mmol) of tricarbonyl(N,N'-diisopropyl-1,4-diazabutadiene)(tetracarbonylcobalt)manganes e (Co—Mn) as a specified substance (yield: 50%).

EXAMPLE 3

A heterogeneous polynuclear complex (dicarbonyl(N,N'-diisopropyl-1,4-diazabutadiene)(tetracarbonylcobalt)methylruthenium (Co—Ru)) having ruthenium as a first transition metal and cobalt as a second transition metal was produced. The synthesis reaction formula is as described below. Hereinafter, the production process will be described in detail.

[Chemical Formula 11]

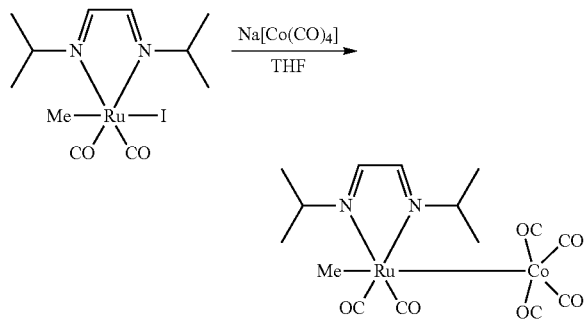

1.71 g (5 mmol) of octacarbonyldicobalt and 0.23 g (10 mmol) of metal sodium were added in a flask containing 250 ml of tetrahydrofuran. The solution was stirred at room temperature for 24 hours, a solution obtained by dissolving 4.39 g (10 mmol) of dicarbonyliodo(N,N'-diisopropyl-1,4-diazabutadiene)methylruthenium in 250 ml of tetrahydrofuran was then added, and the mixture was stirred at room temperature for 4 hours. After completion of the reaction, the reaction product was concentrated to obtain a muddy reaction mixture. The reaction mixture was extracted with hexane, and purified by column chromatography with alumina as a carrier and hexane as an eluent. Sublimation purification was performed to obtain 2.42 g (5.0 mmol) of dicarbonyl(N,N'-diisopropyl-1,4-diazabutadiene)(tetracarbonylcobalt)methylruthenium (Co—Ru) as a specified substance (yield: 50%).

EXAMPLE 4

A heterogeneous polynuclear complex (pentacarbonyl[dicarbonyl(ethyl)(N, N'-diisopropyl-1,4-diazabutadiene)ruthenium]manganese (Mn—Ru)) having ruthenium as a first transition metal and manganese as a second transition metal was produced. The synthesis reaction formula is as described below. Hereinafter, the production process will be described in detail.

[Chemical Formula 12]

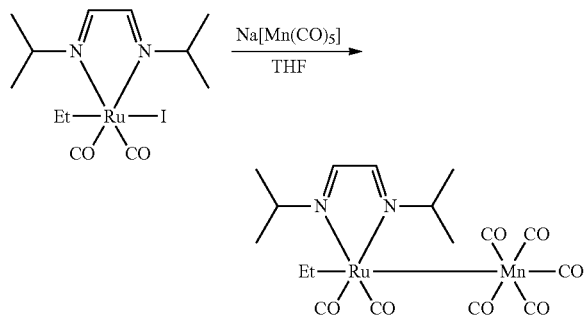

1.95 g (5 mmol) of decacarbonyldimanganese and 0.23 g (10 mmol) of metal sodium were added in a flask containing 250 ml of tetrahydrofuran. The solution was stirred at room temperature for 24 hours, a solution obtained by dissolving 4.53 g (10 mmol) of dicarbonylethyliodo(N,N'-diisopropyl-1,4-diazabutadiene)ruthenium in 250 ml of tetrahydrofuran was then added, and the mixture was stirred at room temperature for 4 hours. After completion of the reaction, the reaction product was concentrated to obtain a muddy reaction mixture. The reaction mixture was extracted with hexane, and purified by column chromatography with alumina as a carrier and hexane as an eluent. Sublimation purification was performed to obtain 2.98 g (5.7 mmol) of pentacarbonyl[dicarbonyl(ethyl)(N,N'-diisopropyl-1,4-diazabutadiene)ruthenium]manganese (Mn—Ru) as a specified substance (yield: 57%).

Evaluation of physical properties of heterogeneous polynuclear complex: Physical properties were evaluated by TG for the heterogeneous polynuclear complexes produced in Examples 1 and 4. Analysis was performed by observing a change in weight of a complex sample (5 mg) in heating of the sample at a temperature elevation rate of 5° C./min over a measurement temperature range, i.e. from room temperature to 450° C., under a nitrogen atmosphere in TG-DTA2000SA manufactured by BRUKER Corporation. For Example 1, analysis (TG measurement under reduced pressure) with a complex sample heated at a pressure of 5 Torr was performed. The results are shown in FIG. 1.

FIG. 1 shows that the complexes in Examples 1 and 4 were vaporized and decomposed by heating at about 130° C., and thus these complexes had a low decomposition temperature, and were capable of forming a film at low temperature. The results of the TG measurement under reduced pressure showed that the complex in Example 1 was totally vaporized without being decomposed at a pressure during film formation.

Film formation test: Next, a film formation test was conducted in which a composite metal thin film was formed by a CVD method with the complex produced in Example 1 as a raw material compound.

Figure 2:
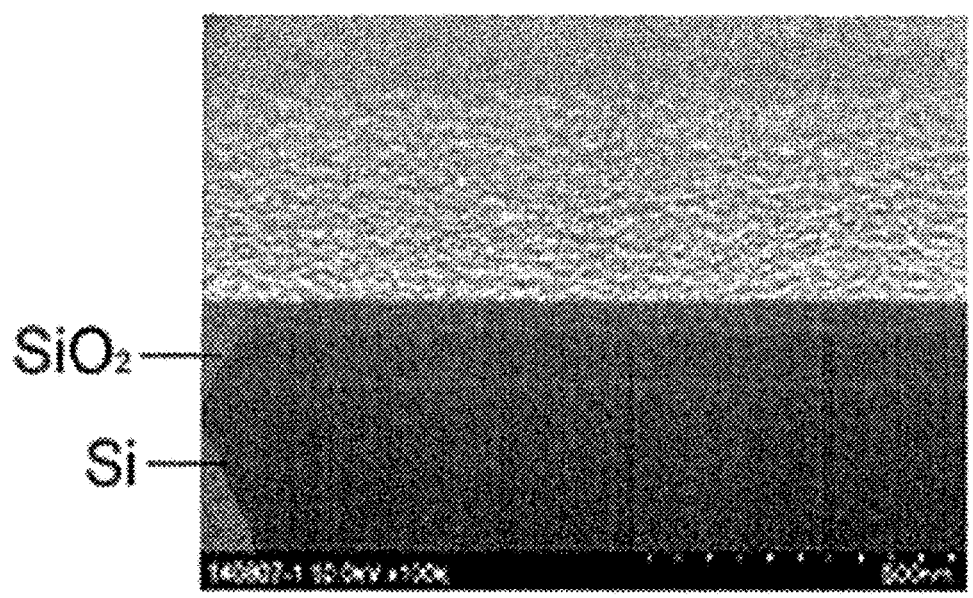
FIG. 2 shows a photograph of a cross-section of a metal thin film formed in an embodiment.

The metal thin film was formed on a substrate (15 mm×15 mm) with a silicon oxide film deposited on a silicon substrate by use of tetraethoxysilane (TEOS). As a film formation apparatus, a hot wall type thermal CVD apparatus was used. A reaction gas (hydrogen) was fed at a constant flow rate by use of a mass flow controller. Film formation conditions are as described below. The result of observing a cross-section of the metal thin film with a SEM is shown in FIG. 2.

Substrate: $SiO_2$
Film formation temperature: 250° C.
Sample temperature: 100° C.
Film formation pressure: 5 torr
Reaction gas (hydrogen) flow rate: 10 sccm
Film formation time: 60 minutes The metal thin film formed in this way was glossy pure white, and had a thickness of 47.2 nm. FIG. 2 shows that the metal thin film formed on $SiO_2$ had a smooth and uniform surface.

Figure 3:
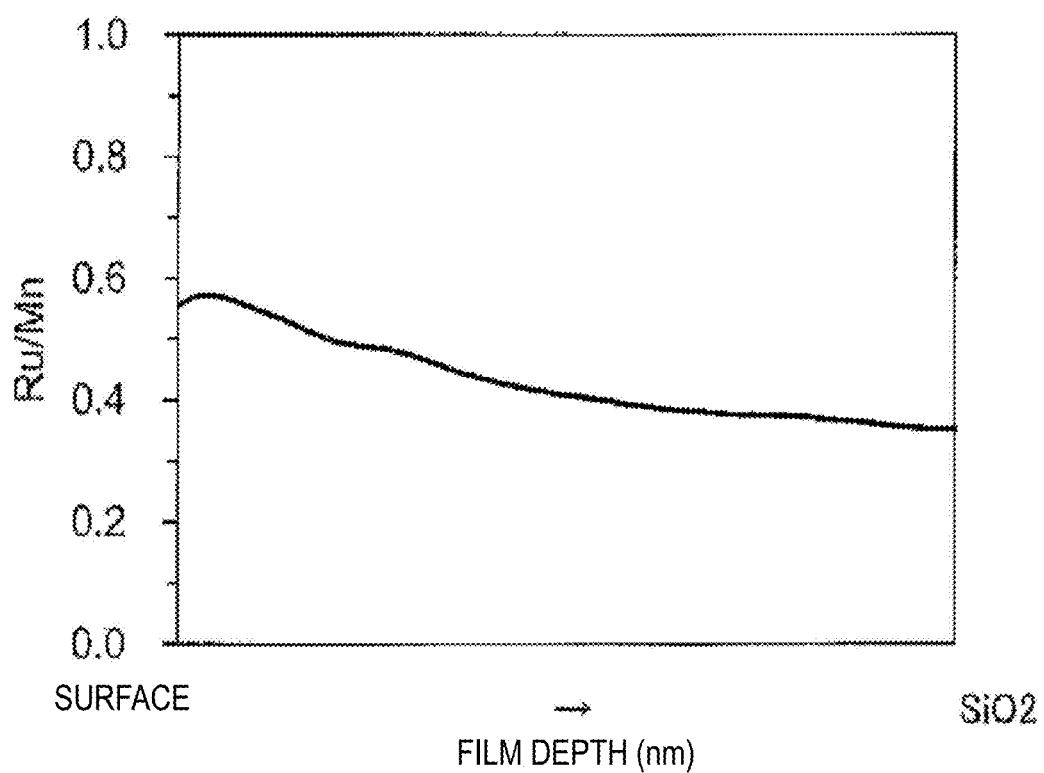
FIG. 3 illustrates a Ru/Mn ratio in a metal thin film formed in an embodiment.

$M_1/M_2$ ratio: the Ru/Mn ratio was analyzed as an abundance of metal elements by an X-ray photoelectron spectroscopy (XPS) method for the metal thin film formed as described above. As a measurement apparatus, KRATOS Axis Nova manufactured by Shimadzu Corporation was used. In this measurement, the thin film (thickness: 47.2 nm) was analyzed in a depth direction from the vicinity of the surface to the upper side of the vicinity of the interface with the $SiO_2$ film. In the vicinity of the interface with the $SiO_2$ film, actions of Si and O made it difficult to correctly analyze the Ru/Mn ratio, and the analysis was performed over a range where the impact was low. The results are shown in FIG. 3. The horizontal axis in FIG. 3 is approximately consistent with a thickness (47.2 nm) from the thin film surface to the upper side of the vicinity of the interface with the $SiO_2$ film.

FIG. 3 shows that both Ru and Mn were deposited in the metal thin film. The Ru/Mn ratio was almost constant (around 0.45) although it tended to be slightly high in the vicinity of the surface of the thin film.

INDUSTRIAL APPLICABILITY

According to the present invention, a composite metal thin film can be formed from a single raw material by a chemical deposition method, and it is easy to make the thin film homogeneous and control quality of raw materials. Thus, the present invention can be applied to uses which employ a structure in which a plurality of metal layers are deposited, such as copper diffusion layers in semiconductor devices.

The invention claimed is:

1. A chemical deposition raw material for producing a composite metal thin film or a composite metal compound thin film by a chemical deposition method, comprising a heterogeneous polynuclear complex in which as ligands, at least a diimine (L) and a carbonyl are coordinated to a first transition metal ($M_1$) and a second transition metal ($M_2$) as central metals, the heterogeneous polynuclear complex being represented by the following formula:

[Chemical Formula 1]

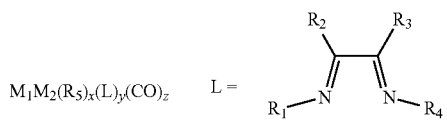

wherein $M_1$ and $M_2$ are different transition metals; x is an integer of 0 or more and 2 or less, y is an integer of 1 or more and 2 or less, and z is an integer of 1 or more and 10 or less; $R_1$ to $R_4$ are each one of a hydrogen atom and an alkyl group with a carbon number of 1 or more and 5 or less; and $R_5$ is a hydrogen atom, a carbonyl, an alkyl group with a carbon number of 1 or more and 7 or less, an allyl group or an allyl derivative.

2. The chemical deposition raw material according to claim 1, wherein x is 1, y is 1 and z is n +2, where n is the number of carbonyl groups bound to second transition metal $M_2$, the chemical deposition raw material comprising a heterogeneous polynuclear complex represented by the following formula:

[Chemical Formula 2]

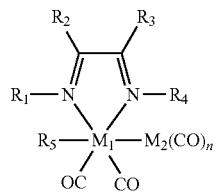

wherein $M_1$ and $M_2$ are different transition metals; n is 3 or more and 6 or less; Each of $R_1$ and $R_4$ is an alkyl group with a carbon number of 1 or more and 4 or less, and each of $R_2$ and $R_3$ is a hydrogen atom, or an alkyl group with a carbon number of 1 or more and 3 or less; and $R_5$ is a carbonyl, or an alkyl group with a carbon number of 1 or more and 4 or less.

3. The chemical deposition raw material according to claim 2, wherein each of $R_1$ and $R_4$ is one of an ethyl group, a propyl group and a butyl group.

4. The chemical deposition raw material according to claim 2, wherein each of $R_2$ and $R_3$ is one of a hydrogen atom, a methyl group and an ethyl group.

5. The chemical deposition raw material according to claim 2, wherein $R_5$ is a carbonyl group, methyl group, ethyl group or propyl group.

6. A chemical deposition method of a composite metal thin film or a composite metal compound thin film, comprising preparing a raw material gas by vaporizing a raw material defined in claim 2 including a heterogeneous polynuclear complex, and heating the raw material gas while introducing the raw material gas to a substrate surface to deposit a composite metal thin film or a composite metal compound thin film.

7. The chemical deposition raw material according to claim 1, wherein the transition metal is one of Mn, Fe, Co, Ni, Cu, Nb, Mo, Ru, Rh, Ta, W, Ir and Pt.

8. The chemical deposition raw material according to claim 7, wherein each of $R_1$ and $R_4$ is one of an ethyl group, a propyl group and a butyl group.

9. The chemical deposition raw material according to claim 7, wherein each of $R_2$ and $R_3$ is one of a hydrogen atom, a methyl group and an ethyl group.

10. The chemical deposition raw material according to claim 7, wherein $R_5$ is a carbonyl group, methyl group, ethyl group or propyl group.

11. A chemical deposition method of a composite metal thin film or a composite metal compound thin film, comprising preparing a raw material gas by vaporizing a raw material defined in claim 7 including a heterogeneous polynuclear complex, and heating the raw material gas while introducing the raw material gas to a substrate surface to deposit a composite metal thin film or a composite metal compound thin film.

12. The chemical deposition raw material according to claim 1, wherein $M_1$ is one of Ru, Mn and Fe, $M_2$ is one of Mn, Fe, Co and Ni, and $M_1$ and $M_2$ are different.

13. The chemical deposition raw material according to claim 12, wherein each of $R_1$ and $R_4$ is one of an ethyl group, a propyl group and a butyl group.

14. The chemical deposition raw material according to claim 12, wherein each of $R_2$ and $R_3$ is one of a hydrogen atom, a methyl group and an ethyl group.

15. A chemical deposition method of a composite metal thin film or a composite metal compound thin film, comprising preparing a raw material gas by vaporizing a raw material defined in claim 12 including a heterogeneous polynuclear complex, and heating the raw material gas while introducing the raw material gas to a substrate surface to deposit a composite metal thin film or a composite metal compound thin film.

16. The chemical deposition raw material according to claim 1, wherein each of $R_1$ and $R_4$ is one of an ethyl group, a propyl group and a butyl group.

17. The chemical deposition raw material according to claim 16, wherein each of $R_2$ and $R_3$ is one of a hydrogen atom, a methyl group and an ethyl group.

18. The chemical deposition raw material according to claim 1, wherein each of $R_2$ and $R_3$ is one of a hydrogen atom, a methyl group and an ethyl group.

19. The chemical deposition raw material according to claim 1, wherein $R_5$ is a carbonyl group, methyl group, ethyl group or propyl group.

20. A chemical deposition method of a composite metal thin film or a composite metal compound thin film, comprising preparing a raw material gas by vaporizing a raw material defined in claim 1 including a heterogeneous polynuclear complex, and heating the raw material gas while introducing the raw material gas to a substrate surface to deposit a composite metal thin film or a composite metal compound thin film.

* * * * *